US005703173A

United States Patent [19]
Koloski et al.

[11] Patent Number: 5,703,173
[45] Date of Patent: Dec. 30, 1997

[54] TRANSITION METALLOHALOPOLYMERS

[75] Inventors: Timothy S. Koloski; Terrence G. Vargo, both of Kenmore, N.Y.

[73] Assignee: Integument Technologies, Inc., Jamestown, N.Y.

[21] Appl. No.: 689,707

[22] Filed: Aug. 16, 1996

[51] Int. Cl.$^6$ .................................................. C08F 81/42
[52] U.S. Cl. ................................. 525/326.2; 525/326.4
[58] Field of Search ......................... 525/326.2, 326.4

[56] References Cited

U.S. PATENT DOCUMENTS

| | | | |
|---|---|---|---|
| 4,080,490 | 3/1978 | Dawans et al. | 525/326.2 |
| 4,946,903 | 8/1990 | Gardella et al. | 525/326.4 |
| 5,051,312 | 9/1991 | Allmer | 428/458 |
| 5,266,309 | 11/1993 | Gardella et al. | 424/78.09 |

OTHER PUBLICATIONS

Olah, George A., et al; *Superacids*, John Wiley & Sons; 1985, pp. 53–64 and 145–160.
Campbell, Ian M.; *Catalysis at Surfaces*, Chapman and Hall; 1988, pp. 64–68.
Allmer, Klas, et al; *Photochemical Modification of a Fluoropolymer Surface*, Macromolecules, vol. 24, No. 19, 1991, pp. 5487–5488.
Drago, Russell S.; *Homogeneous metal–catalyzed oxidations by $O_2$*, Coordination Chemistry Reviews, 117 (1992) pp. 185–213.
Vargo, Terrence G., et al; *Adhesive Electroless Metallization of Fluorpolymeric Substrates*, Science 1993, vol. 262, pp. 1711–1712.

Hung, Ming–H., et al; *Functionalization and Metallization of Fluropolymer Surfaces Through Reduction*, Journal of Applied Polymer Science, vol. 55, pp. 549–559 (1995).

*Primary Examiner*—Ralph H. Dean
*Attorney, Agent, or Firm*—Howard M. Ellis; Marianne Fuierer

[57] ABSTRACT

Novel metallohalopolymers comprising an oxyhalopolymer and a transition metal covalently bonded to an oxygen site on the oxyhalopolymer possess desirable properties of inertness, stability, hydrophobicity and high electronegativity like fluoropolymers such as PTFE. The metallohalopolymers also possess unusual superacidic properties making oxygen-containing sites on the polymeric backbone highly nucleophilic and reactive with transition metals for synthesis of stable metallized polymers without requiring exposure to destructive calcining temperatures or intermediate chelating organosilane linking agents. The transition metals can be covalently bonded directly to the polymeric support to form metallohalopolymers for use as catalysts in the synthesis of chemicals, biocides and useful articles of manufacture, such as filtration devices containing the biocidally active metallohalopolymers.

31 Claims, No Drawings

TRANSITION METALLOHALOPOLYMERS

TECHNICAL FIELD

The present invention relates generally to novel metallohalopolymers, methods of making and articles of manufacture. More specifically, the invention relates to highly electronegative bulk polymers having transition metal ions or conductive transition metallic films (i.e., transition metals in a zero oxidation state) covalently bonded directly to the base polymer, methods of making, compositions of matter and devices comprising the same. The transition metals are linked to the polymers by either gas phase or solution phase chemistries allowing control over the oxidation state of the metals to produce unique materials with utilities, such as heterogeneous catalysts for the synthesis of chemicals, solid biocides and as useful articles of manufacture, e.g., filtration devices containing the biocidally active metallohalopolymers.

BACKGROUND OF THE INVENTION

Fluoropolymers and fluorochloropolymers, such as fluorohydrocarbon polymers, e.g., polyvinylidene fluoride (PVDF), polyvinyl fluoride (PVF), polychlorotrifluoroethylene (PCTFE), including the well known fluorocarbon polymers, e.g., perfluorinated polymers, like polytetrafluoroethylene (PTFE), and expanded polytetrafluoroethylene (ePTFE), are characterized by extreme inertness, high thermal stability, hydrophobicity, low coefficients of friction and low dielectric properties. While these properties are highly desirable for many applications, it would also be advantageous to not only retain them, but also utilize their highly electronegative characteristics for enhancing the properties of transition metals by covalently bonding transition metals to active sites generated on the polymer surfaces.

Other classes of perfluorinated polymers with ion exchange properties have been synthesized such that they contain sulfonic acid sites (many of which are commercially available under such names as Nafion®, a trademark of E. I. DuPont) or carboxylic acid sites within the resin matrix. Because of the electronegative properties imparted by the fluorine and chlorine atoms of these materials, the acid sites synthesized on these polymers possess unique superacidic properties, i.e., acidity sufficiently great to donate a proton to molecules or substances having the acidic properties of sulfuric acid. Representative examples of superacids include fluorosulfonic acid and trifluoromethanesulfonic acid, both of which exceed the acidity of sulfuric acid, i.e., capable of donating a $H^+$ to sulfuric acid. Certain superacidic materials have been shown to be useful in acid catalyzed hydrocarbon conversion processes to isomerization, cracking or alkylation-homologation products, acid catalyzed acylation of aromatic compounds, acid catalyzed carboxylation, and so on.

In addition to the foregoing applications, perfluorosulfonic acid polymers like Nafion have also found extensive use in electrolytic cells as ion exchange membrane type separators, in fuel cells and as heterogeneous catalysts. Notwithstanding their desirable superacidic properties, perfluorosulfonic acid resins, carboxylic acid resins, etc., have limitations due to their inability to form stable covalent bonds with metals. In addition, because of the method for their synthesis polymers of this family of materials have substantially similar physical and chemical properties, e.g., reactivity, wettability, adhesion characteristics, porosity, tensile strength, optical transparency, and so on. Consequently, perfluorinated ion exchange resins have not been synthesized with desirable properties like PVDF, the latter of which can be fabricated to include piezo and pyroelectric properties, or ePTFE with pore sizes that can be controlled for use in a variety of filtration applications.

Certain fluoropolymers have been modified through refunctionalization by the introduction of alkali metals. They are described in U.S. Pat. No. 5,266,309 by J. A. Gardella and T. G. Vargo. In this invention, the surface fluorine atoms of a fluoropolymer to depths from about 10 to about 100 Å are permanently substituted with hydrogen and oxygen or oxygen-containing groups of which from about 3 to about 30 percent of the substituted fluorine is replaced with oxygen or oxygen-containing groups and from about 70 to about 97 percent of the substituted fluorine is replaced with hydrogen atoms. The oxyfluoropolymers are refunctionalized by ionically bonding from about 3 to about 100 percent of the oxygen or oxygen-containing groups to alkali metals, like sodium, potassium and lithium. These permanently modified metallized oxyfluoropolymers find wide ranging applications, including such representative uses as filtration membranes, in the fabrication of prosthetic devices, bioprobes, and in a variety of other applications where it is desirable to retain the morphological and hydrophobic properties of the starting fluoropolymer, i.e., the ability to repel water and other polar solvents having high surface tensions, i.e., >50 dynes/cm, including high thermal stability, low adhesion, dielectric properties and low friction coefficients, while also increasing the surface free energy and wettability properties with respect to low surface tension liquids, i.e., <50 dynes/cm, such as with non-polar organic solvents, blood plasma, etc.

The introduction of ionically bonded alkali metals directly to the above oxyfluoropolymers is readily achieved due to the low ionization potential for such metals. This allows alkali metals to readily react by forming ionic salts with negative ionic sites on the base polymer, e.g., oxygen functionalities. However, the introduction of transition metals onto oxyfluoropolymeric sites, unlike alkali metals, is more problematical. This is because of a substantially different bonding mechanism required with transition metals.

Heretofore, catalytically active oxyhalopolymers having transition metals covalently bonded directly thereto have not been plausible. This is because direct bonding of transition metals to solid supports requires severe reaction conditions. For instance, G. A. Olah, et al report in their text, *Superacids*, P. 58, John Wiley and Sons, Inc. (1985) reactions which first require deprotonation of alcohol functionality through high temperature activated dehydrolysis. The temperatures necessary for achieving the initial dehydrolysis and the subsequent reaction of the electron seeking transition metal to the nucleophilic oxygen atom activated on these surfaces are on the order of several hundred degrees higher than the temperatures at which base fluoro- or fluorochloropolymers decompose. Such elevated temperatures will degrade or at least permanently modify the polymer causing it to lose its desirable properties. Hence, the inability to successfully synthesize halopolymers metallized directly with transition metals has deterred their development.

Efforts to metallize oxyfluoropolymers with transition metals have been reported by T. G. Vargo, et al in *Science*, 10 Dec. 1993, Vol. 262, 1711–1712. This paper discloses fluoropolymers metallized with conductive, zero valent coatings of palladium or nickel. More specifically, fluoropolymers, such as FEP are hydroxylated by radio frequency glow discharge (RFGD), refunctionalized by chemisorption of an organosilane, followed by application of an adherent metal deposit by ligand based electroless metal deposition. The metallic coatings are applied after the polymer has been refunctionalized with an aminoalkylsilane. According to the authors, the transition metals are not directly bonded to the oxygen sites of the base polymer, but instead applied through the coordinate covalent bonding of a Pd-based precursor to the amine functionality contained in the aminosilane intermediate coupling agent. This intermediate coupling method has certain shortcomings including the formation of reversible coordinate covalent bonds with the Pd-based precursor used for initiating electroless metallization. Such bonds have been found to lack stability, break and eventually leach off polymer surfaces with exposure to varying temperature conditions, solvents and pH.

Accordingly, it would be highly desirable to have a group of novel bulk metallohalopolymers possessing all the desired properties of inertness, stability, hydrophobicity and high electronegativity of fluoropolymers like PTFE, and which also possess the superacidic characteristics of a perfluorosulfonic acid resin, like Nafion, but which are capable of forming stable, covalent bonds directly with a wide range of transition metals for applications ranging from broad spectrum biocides to catalysts for the synthesis of organic molecules and industrially relevant chemicals.

SUMMARY OF THE INVENTION

In accordance with the invention metallohalopolymers, methods of making, compositions of matter and articles of manufacture are provided. The metallohalopolymers are characterized by a high degree of inertness, high thermal stability, low dielectric properties, while also retaining high electronegativity for enhanced performance as solid heterogeneous catalytic materials. In addition to the foregoing, the metallohalopolymers possess superacidic properties and form stable covalent bonds directly with transition metals to form catalytically active sites on polymer surfaces without degrading or adversely modifying the native properties of the polymer, and to form an improved new class of transition metal heterogeneous catalysts without requiring intermediate coupling agents.

Hence, the invention contemplates a novel series of polymeric supports having significantly overall improved properties as solid substrates, especially for heterogeneous catalysis with characteristics which include (i) sterics that are associated with solid supports; (ii) highly electron withdrawing bulk properties; (iii) a new class of heterogeneous catalysts with high surface areas, including materials prepared from such starting polymers as ePTFE or PTFE; TFE; PCTFE, FEP, PFA and PTFE beads or other particles; (iv) metallohalopolymers possessing excellent thermal and physical properties which make them robust and stable under pressures and temperatures significantly higher than other polymeric supports for heterogeneous catalysis, and (v) the ability to achieve high densities of reactive sites capable of covalently bonding directly with high surface concentrations of transition metals.

It is therefore a principal object to provide a series of novel metallohalopolymers possessing the foregoing properties, comprising a halopolymer. Typically this would include perhalocarbon polymers and halohydrocarbon polymers. The halopolymer is modified by substituting hydrogen and oxygen or oxygen-containing groups for at least a portion of the halogen atoms of the halopolymer to provide an oxyhalopolymer. Preferred oxyhalopolymers are selected from the group consisting of oxyfluoropolymers and oxychlorofluoropolymers. The sites of the oxygen or oxygen-containing groups on the oxyhalopolymer are modified with controlled amounts of a transition metal covalently bonded directly thereto to provide surfaces having catalytic activity with about the same physical properties, and with electron withdrawing characteristics corresponding substantially with those of the starting halopolymer. Generally, transition metals for this invention are intended to include metals from Groups IIIa, IVa, Va, VIa, VIIa, VIIIa, Ib, IIb, IIIb and IVb. Thus, a principal aspect of the invention is an improved class of metallohalopolymers comprising an oxyhalopolymer and a transition metal covalently bonded directly to an oxygen site on the oxyhalopolymer.

It is yet a further object of the invention to provide for metallohalopolymers in which the oxygen-containing groups are modified with covalently bonded transition metal ions or covalently bonded conductive metallic film in which many of the properties native to the starting fluoropolymers are retained. In one representative embodiment of the invention from about 1 percent to about 100 percent of the surface oxygen or oxygen-containing functionalities of the oxyhalopolymer to depths ranging from about 10 to about 200 Å have transition metals covalently bonded directly thereto. Accordingly, the invention contemplates from minor to major amounts of the fluorine atoms of the starting fluoropolymer being substituted with hydrogen atoms and oxygen atoms or low molecular weight oxygen-containing functionalities. These oxygen sites have covalently bonded transition metals, including elements 21 through 29 (scandium through copper), elements 39 through 47 (yttrium through silver), elements 57 through 79 (lanthanum through gold), and all known metals from actinium (89), and so forth.

A further preferred embodiment of the foregoing invention includes metallohalopolymers wherein from about 1 to about 90 percent of the surface halogen atoms, particularly to depths from about 10 to about 200 Å are substituted with hydrogen and oxygen or oxygen-containing functionalities wherein from about 30 to about 100 percent of the substituted halogens are replaced with oxygen or oxygen-containing groups and from about 0 to about 70 percent of the halogens are replaced with hydrogen atoms, and where from about 1 to about 100 percent of the surface oxygen or oxygen-containing groups have covalently bonded directly thereto a transition metal from the above groups.

It is still a further object of the invention to provide metallohalopolymers comprising an oxyhalopolymer prepared from a perhalocarbon polymer or a halohydrocarbon polymer. Representative oxyhalopolymers are those selected from the group consisting of an oxyfluoropolymer and an oxychlorofluoropolymer wherein at least a portion of the oxygen or oxygen-containing groups of the oxyhalopolymer have covalently bonded directly thereto a transition metal or covalently bonded conductive metallic film in a sufficient amount to provide a metallohalopolymer possessing catalytic properties. The thermal stability and electron withdrawing characteristics of the metallohalopolymer correspond substantially to the starting perhalocarbon polymer or halohydrocarbon polymer.

A further object of the invention also includes methods for synthesizing the previously described metallohalopolymers by the steps of:

(a) providing a halopolymer selected from the group consisting of a perhalocarbon polymer and a halohydrocarbon polymer;

(b) modifying the halopolymer of step (a) by treating by a step selected from the group consisting of (i) a radio frequency glow discharge hydrogen/methanol gas-vapor under vacuum, (ii) wet chemical reduction and (iii) exposure to actinic radiation in the presence of oxygen-containing organic modifiers to substitute at least a portion of the halogen atoms with hydrogen and oxygen or oxygen-containing groups at the molecular level to provide an oxyhalopolymer selected from the group consisting of an oxyfluoropolymer and oxychlorofluoropolymer, and (c) contacting the oxyhalopolymer of step (b) with either a solution or vapor comprising transition metal complexes for a sufficient time period to facilitate covalently bonding directly thereto of a transition metal or covalently bonded conductive metallic film in a controlled amount to provide a metallohalopolymer possessing catalytic properties, and wherein the thermal stability and electron withdrawing characteristics of the metallohalopolymer correspond substantially to that of the starting halopolymer.

It is still a further object of the invention to provide compositions of matter comprising the metallized highly electronegative bulk halopolymers, and particularly fluoropolymers or fluorochloropolymers (metallohalopolymers) for use in heterogeneous catalysis, and as broad spectrum biocides. Generally, the transition metal complexes used in this invention are useful in both homogeneous and heterogeneous catalysis, but are especially adaptable as heterogeneous metallic catalysts in the synthesis of chemicals. In addition certain metallohalopolymeric compositions of the invention are also active as biocides, i.e., effective in a biological system by demonstrating fungicidal, bactericidal, viricidal activity, and so on. As a result, certain metallohalopolymers can be employed in various systems, such as filtration devices for purification of gases and liquids. The metallohalopolymers may also be employed in sensor probes.

DESCRIPTION OF THE PREFERRED EMBODIMENTS

Through various liquid and gas/vapor phase, e.g., CVD (chemical vapor deposition)chemical reactions, methods are described which provide for metallized polymers comprising transition metal species covalently bonded directly to partially halogenated polymeric supports, e.g., fluoropolymeric, chlorofluoropolymeric, etc., solid substrates. The transition metals are bonded to the halogenated polymers to provide compositions of matter comprising base halogenated polymers with the metals covalently bonded to surface oxygen functionality to depths of approximately 200 Å. In this regard, while the invention contemplates oxygen or oxygen-containing functionalities at the surface to be metallized, the metallohalopolymers likewise may have their oxygen or oxygen-containing groups at the top 10 Å to about 200 Å of the starting polymeric material to also be metallized. This will form a molecular layer of the transition metal covalently bonded to the oxygen sites, or multimolecular film of transition metal from 10 Å to more than a micron thickness stabilized by an initial molecular layer of transition metal. The new metallized polymers of this invention may hereinafter be referred to as metallohalopolymers or "MHPs".

Representative MHPs may include the following structural formulas with repeating non-terminal units selected from the group of:

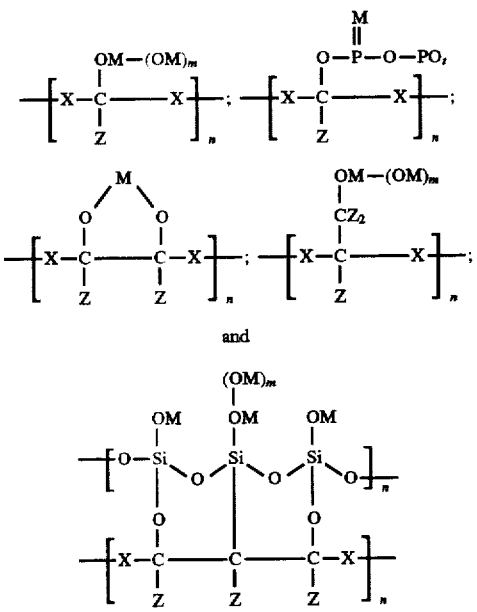

Wherein M is a transition metal; Z is fluorine, chlorine, hydrogen, —(CH$_2$)$_y$—CH$_3$, —CH$_3$ or O—R where R is hydrogen, —(CH$_2$)$_y$—CH$_3$ or —CH$_3$ where y is 1 to 20; X is CF$_2$, CFCl, CCl$_2$, CFH, CClH or CH$_2$ or CH$_2$ and n=10 to 1000, t=2 to 3 and m=0 to 1000.

For purposes of this invention, expressions, such as "halogenated polymers", "halopolymers" and variations thereof as used in the claims and disclosure are intended to mean polymeric materials containing highly electronegative atoms referred to in the elemental periodic table as halogens, i.e.,fluorine, chlorine, bromine, and iodine. The halogenated polymers preferred as starting materials for this invention are those comprised of a carbon backbone, with practically any combination of fluorine, chlorine, hydrogen, and oxygen atoms attached thereto. This includes polymeric carbon backbones containing one or any combination of two, three or four atoms out of the group of fluorine, chlorine, hydrogen and oxygen. For example, fluoro- and fluorochloropolymers, such as fluorohydrocarbon polymers like polyvinylidene fluoride (PVDF), polyvinyl fluoride (PVF), polychlorotrifluoroethylene (PCTFE), polytetrafluoroethylene (PTFE), fluorinated ethylene propylene copolymer (FEP), expanded polytetrafluoroethylene (ePTFE), and polyvinyl chloride (PVC) are, although not totally inclusive, all illustrative of starting halogenated polymers having carbon and fluorine atomic compositions, as well as polymers having carton and chlorine; carbon, fluorine and chlorine; and carbon, fluorine and hydrogen. That is, they are generically known as halocarbon and halohydrocarbon polymers. Other halogenated polymers serving as useful starting materials include the various perfluorinated and halogenated siloxanes copolymers comprised of tetrafluoroethylene block segments with other non-halogenated polymeric blocks e.g., polytetrafluoroethylene-ether-urethane (PFEU) and polyfluoroalkoxy polymers or copolymers comprising tetrafluoroethylene and perfluoro-2-2-dimethyl-1,3-dioxole e.g., Teflon-AF®, a Dupont trade-mark, perfluorinated polystyrenes and copolymers containing fluorinated styrene segments, fluorinated phosphazines, as well as the myriad of other polymeric materials containing halogenated functionality which can be segregated and exposed at the surface of the material creating a highly electronegative environment.

As previously indicated, in preparing the MHPs, useful starting materials include the halogenated polymers cited above which are treated such that incorporation of reactive oxygen functionality to the molecular structure of the halogenated polymer is readily accomplished. The objective is to introduce either oxygen or oxygen-containing groups onto the halopolymeric material and thereby displace some of the halogen atoms to form a stable intermediate material. This does not include the introduction of oxygen atoms into the polymer backbone per se, but only in substituting existing halogen atoms. The oxygen functionality may be varied and include such representative examples as hydroxyl (—OH), ether (C—O—C), epoxide (—O—), aldehyde (—HC=O), ester (O=C—O—) or carboxylic acid (—COOH). These oxygen functionalities have the desired electronic characteristics and chemical reactivity required according to this invention. Specifically, these oxygen functionalities when incorporated onto the carbon backbone of a polymer which also contains electronegative atoms, such as fluorine or chlorine (or functional groups containing these atoms) have properties similar to Bronstead acids (e.g. in the cases of hydroxyl and the carboxylic acid functionality) or, Lewis bases which are able to donate lone pairs of electrons in the cases of the epoxide, aldehyde, ester and ether functionalities. Further, we discovered that these surfaces have properties similar to those found in materials defined previously as solid superacids (see pgs 145–160 in *Catalysis at Surfaces*, by Ian M. Campbell, published by Chapman and Hall 1988) in our invention.

For purposes of this invention expressions like "solid superacids" or "superacidity" or variations thereof, are intended to mean polymeric surfaces having stronger acidities than that of concentrated sulfuric acid (18 Molar). In the case of the MHPs of this invention, the oxygen functionality used to covalently bond transition metals to halopolymeric surfaces are capable of protonating $H_2SO_4$ to $H_3SO_4^+$ in cases where the oxygen functionality is either an alcohol or a carboxylic acid. Two representative examples of known solid superacids which have similar superacidic properties, but different physical properties to the superacidic materials described herein include the class of perfluorinated sulfonic acid ion exchange polymers (Nafion® brand polymers) and alumina-silica mixtures doped with antimony pentafluoride ($SbF_5$). For a more complete listing and description of superacids and solid superacids which are related to the starting fluoropolymer reactants for this invention see Superacids, by, G. A. Olah, G. K. Surya Prakash, and J. Sommer, published by John Wiley and Sons, Inc., 1985, the contents of which are incorporated herein by reference.

The superacidic properties of the MHPs are believed specially significant with respect to the novel solid heterogeneous catalysts of the invention. First, the actual observation of superacidic properties on these MHPs represents a novel class of solid superacids possessing similar catalytic properties as compounds heretofore known as solid superacids, which are capable of converting or isomerizing alkanes and promoting acid catalyzed electrophilic reactions (see Olah et. al.,supra, pg 53–64). Secondly, due to the chemical nature of these superacidic oxygen sites, the stable covalent bond coupling of transition metals can be facilitated. Thirdly, because of the electron withdrawing nature of the superacidic oxygen sites of the MHPs of this invention, the covalently bonded transition metals experience a large delocalization of their electrons which is believed to enhance the catalytic activity of the bonded transition metals.

Our discovery of the unique reactivity (i.e., superacidic characteristics) of the oxyhalogenated surfaces has enabled the covalent bonding of transition metals directly to the polymeric substrate. The resulting MHP surface and its ability to perform as a heterogeneous catalytic support, biocidal filter, sensor, etc., are dependent on such variables as particular transition metal employed, stability required, desired oxidation state of the metal, the amount and type of oxygen functionality incorporated at the surface of the halogenated polymer.

In general, the incorporation or synthesis of oxygen sites on the surface of a halogenated polymer need only be of such concentration that the oxygen functionality and resulting backbone of the polymer be stable. Typically, this would range from about 3 to about 70 percent of the original halogens of the fluoropolymer being substituted with oxygen or oxygen-containing groups. In addition to those mentioned above, oxygen functionality may take the form of oxo, hydroxyl, alkoxy, inclusive of methoxy, ethoxy and propoxy or R'—CO— or combinations thereof, where R' is hydrogen or alkyl, and particularly C1 to C5 lower alkyl, including methyl, ethyl, propyl, isopropyl, and so on. In addition, the oxygen functionality may also take the form of $PO_y$ or $SiO_y$, wherein y is 2–3 as disclosed hereinabove. One representative example of means for preparing fluorinated polymers with the desired oxygen functionality has been demonstrated by J. A. Gardella, Jr. and T. G. Vargo in U.S. Pat. Nos. 4,946,903 and 5,266,309, the disclosures of which are incorporated herein by reference. According to Gardella and Vargo, oxygen functionality can be incorporated into fluorinated polymers and resins by exposing them to a RFGD plasma comprised of a $H_2$/MeOH mixture, for example. Using this procedure it has been shown that hydroxyl functionality can be permanently formed onto fluoropolymeric surfaces, such as FEP, PTFE, ePTFE, and PVDF. Accordingly, the RFGD methods of Gardella and Vargo provide but one useful means for producing surfaces having the appropriate superacidic characteristics for preparing the MHPs of the invention.

Other means for introducing superacidic oxygen functionality onto starting halogenated polymers may include those disclosed by U.S. Pat. No. 5,051,312 (K. J. M. Allmer), the contents of which is incorporated herein by reference. The methods of Allmer provide for the introduction of oxygen functionality onto the halogenated polymer via simultaneous exposure of the polymer to actinic radiation, e.g. UV, X-ray, or e-beam, which is absorbed by an organic compound referred to as a "modifier". Representative examples of useful "modifiers" include sodium 4-aminothiophenoxide (SATP), sodium benzhydroxide (SBH), and disodium 2-mercapto-3-butoxide (DDSMB), all of which are strong reducing agents for facilitating hydrogen abstraction in the presence of actinic radiation. Essentially, a halogenated material is immersed into one of the prescribed organic "modifiers" and simultaneously exposed to actinic radiation, such as UV radiation for a prescribed length of time.

In sum, methods of the invention contemplate virtually any suitable technique for modifying halogenated polymers through the introduction of oxygen-containing sites for covalent bonding with transition metals, including covalently bonding metals to oxygen or oxygen- containing functionalities in proximity to sites of high electronegativity for producing polymers possessing enhanced levels of performance.

The metals are capable of being covalently bonded in controlled amounts, and with predetermined valences. The concentration of transition metal introduced into the polymer may be controlled, for example, by kinetics where the reaction speed depends on a variety of conditions including, (i) the solution chemistry utilized; (ii) the binding strength of the ligand on the organometallic complex starting material which is dissociated during the reaction to form the MHP, and (iii) the use of gas phase as opposed to solution phase (e.g., solution phase could react to form metallooxo functional groups at the oxyfluoropolymer surface whereas a chemical vapor deposition could react to form both a metallooxo bond plus deposit an additional overlayer of metal onto the metallooxo functionality).

Alternatively, metal concentration of the MHP may be controlled by the amount of oxygen functionality initially present in the starting oxyfluoropolymer material which can be controlled by methods described in U.S. Pat. Nos. 4,946,903; 5,051,312; and 5,266,309.

Methods for controlling the oxidation state of the metal of the MHP are also varied. For instance, one can construct a $Rh^{+3}$ MHP according to the invention by depositing rhodium from an aqueous solution containing $RhCl_3$ wherein the oxidation state of the rhodium in the starting organometallic complex is +3. Alternatively, a $Rh^0$ MHP can be made by depositing $RhCl_3$ from a solution containing ethanol. In this case, the $Rh^{+3}$ of the starting organometallic complex is reduced by the presence of alcohol during the reaction to the oxyhalopolymer in order to form the $Rh^0$ MHP. Thus, in this case control of the oxidation state may be achieved by adding an appropriate reducing agent to the reaction solution which will effectively lower the oxidation state of the starting metal contained in the organometallic starting material.

In general, the oxidation state of the metal contained in the organometallic starting material can be preserved and thus, further controlled by choosing an organometallic starting material containing the transition metal in the desired oxidation state. Thus, for example, to make a MHP with $Cu^{+2}$, a $CuCl_2$ organometallic starting material could be reacted with an oxyfluoropolymer by exposing the oxyfluoropolymer to a millimolar solution of $CuCl_2$ in DMF. A $Cu^{+1}$ MHP could be prepared by exposing an oxyfluoropolymer to a millimolar solution of CuSCN in 0.5M $NH_4OH$. $Cu^0$ MHP may be prepared by adding an effective reducing agent to the reaction solutions or by immersing $Cu^{+1}$ or $Cu^{+2}$ MHP materials in a bath containing an appropriate reducing agent for copper such as $NaBH_4$.

A further alternative for controlling the oxidation state of the transition metal of the MHPs of this invention comprises utilizing the strength of the ligands making up a particular organometallic complex starting material. For example, $Cr(CO)_6$ (chromium hexacarbonyl) represents Cr in a zero oxidation state. The carbonyl ligands are relatively weakly bound, so that all six of them can be liberated during the reaction to an oxyfluoropolymer to yield a $Cr^{+6}$ MHP. Alternatively, tristrialkylphosphine Chromium(III) chloride ($(PR_3)_3\ CrCl_3$) comprises three labile chlorine ligands and three relatively stable trialkylphosphine ligands which upon reacting with an oxyfluoropolymer result in the Cr losing the three chlorine ligands while retaining the three trialkylphosphines; thus resulting in a $Cr^{+3}$ MHP.

Metallization of the oxyhalogenated polymer can be either over the entire exposed surface, to selected regions or applied in predetermined patterns. That is to say, before metallization the starting fluoropolymer can have highly reactive oxygen functionalities introduced to the entire exposed surface of the oxyhalopolymer or to selected sides or regions. Because of uniform, nondiscriminatory introduction of oxygen functionalities in place of some or most of the halogen atoms the oxyhalocarbon or oxyhalohydrocarbon polymeric supports can then be uniformly metallized with covalently bonded transition metal ions or covalently bonded conductive metallic films by known methods, such as electroless metal deposition. Such methods do not require exposing the polymers to degrading calcining temperatures. Our recognition of the enhanced nucleophilic properties of the foregoing oxyhalopolymers due to their superacidic characteristics has made possible, for the first time, electroless covalent bonding of transition metals directly through the oxygen sites on solid polymeric supports.

In addition to the above methodology, a solid polymeric support can be selectively metallized through the introduction of reactive oxygen sites using known masking techniques. With a template type system, only the exposed or unmasked portions of the polymeric support will be oxyhalogenated and ultimately metallized for a patterned effect. Further, the invention contemplates, depending on the degree of electronegativity (which is dependent on the concentration of halogenated functionality in proximity to the covalently bonded metal), enhancing and controlling the catalytic activity of the metal with regard to its function, i.e., as a catalyst, biocide, or sensor.

While not wishing to be held to any specific mechanism of action, it is nevertheless believed that covalent bonding of metals directly to oxygen functionality without the usual application of degrading calcining temperatures or organic crosslinking molecules or films is achieved through the electronic environment of the substrate. For example, the superacidic properties of the polymeric support allow for nucleophilic displacement of selected ligands from a transition metal inorganic complex, thus facilitating covalent bonding of the metal to the oxygen sites on the polymeric support.

Although this invention pertains to the covalent bonding of transition metals which have catalytic activity useful for heterogeneous catalysis, sensor and filter applications, it is to be understood that each transition metal has unique characteristics for catalyzing different kinds of synthetic reactions, and thus can be considered for a myriad of technologies related to the described applications. For example, Fischer-Tropsch synthesis (FTS) of hydrocarbons was stimulated in 1974, when the oil supply crisis relied heavily on the hydrogenation of CO to $CH_4$. The pattern of transition metals within the transition metal periods of the Periodic Table shows varying activities of these metals for performing FTS. A complete and definitive description of various transition metals and their utility for FTS is given in Studies in Surface Science and Catalysis 79, "Catalysis", An Integrated Approach to Homogeneous, Heterogeneous and Industrial Catalysts, Eds. J. A. Moulijn, P. W. N. M. van Leeuwen, R. A. van Santen, Elsevier Science Publishers B. V. 1993.

As a further example, the catalytic oxidation of sulphur dioxide to sulfuric acid and ammonia to nitric acid are extremely important industrially based processes. Oxidative catalysis of ethylene and propylene epoxides and phthalic anhydrides among others are also examples of relevant industrially based catalytic conversions of alkanes by oxidative catalysis. A list of relevant oxidative catalytic based syntheses of important industrial materials is given in Chapter 5, pg 187 of Studies in Surface Science and Catalysis 79, "Catalysis", An Integrated Approach to Homogeneous, Heterogeneous and Industrial Catalysts, supra. This publication lists the usefulness but different catalytic utilities for Pt, Rh, V, Cu, Fe, Ag, Al, Hg, Mo, Ti, Pd, and Zr. All of these metals are contemplated within the scope of this invention as being useful when bonded to oxyhalogenated polymers which preserves, and in some cases, enhances their catalytic activity.

The foregoing are but a few examples of many made possible by this invention. It has also been shown that transition metals like Ag, Cu, and Zn, have appropriate redox potentials which allows them to cycle their oxidation state in a manner which can be effectively used to kill bacteria and viruses. The silver and copper containing MHPs provide bactericidal and viricidal activity to the compositions of this invention which are useful as biocides in air and water filtration systems, for example.

Nearly all catalytic reactions involve "oxidative addition" and "reductive elimination" cycles in which the transition metal cycles between low and high oxidative states. Thus, for purposes of this invention the only requirement for fabricating a useful heterogeneous catalytic support is that a transition metal be bonded to a surface such that the metal is bonded in an appropriate oxidation state that facilitates catalytic activity through the cycling mechanism as described. A good reference which describes the cycling mechanism of catalytic transition metals for synthesizing various products can be found in any advanced inorganic chemistry text, like *Advanced Inorganic Chemistry*, 4th edition by F. A. Cotton and G. Wilkinson, John-Wiley and Sons 1980, the contents of which are incorporated herein by reference. For example, the hydrogenation of unsaturated organic compounds using $(PPh_3)_3RhCl$ is described and typically referred to as Wilkinson's catalyst.

As previously pointed out, the metallohalopolymers of the invention are useful in fabricating articles of manufacture, including but not limited to sensor devices. Because of the physical and chemical inertness of halopolymers, in particularly fluoropolymers, they can be stable at temperatures well above those of most conventional polymeric materials used in sensor applications. Significantly, the MHPs of this invention resist weathering and fouling in conjunction with possessing catalytic activity.

Heretofore, oxyfluoropolymers synthesized from ePTFE and FEP have been demonstrated as being useful substrates for immobilizing biological recognition elements which were then used for the construction of high performance fiber-optic based immunoprobes or sensors (F. V. Bright et. al., *Anal. Chim. Acta*, 262 (1992) 323.). The enhanced performance of such sensors was directly related to the non-fouling characteristics of the modified ePTFE and FEP oxyfluoropolymeric supports onto which the recognition elements were covalently bonded.

The MHP's, as described herein, offer similar advantages (e.g., non-fouling characteristics) in conjunction with catalytic activity. For example, a fiber-optic based sensor similar to the design described in Bright et. al. utilizes a fiber-optic tube which first carries radiation of a particular wavelength through the fiber-optic to the distal end which employs a material (either quartz or FEP) which acts as a window through which radiation can exit and enter. The radiation wavelength is chosen such that it is useful for exciting and causing particular molecules of interest to fluoresce. The fluorescence is then carried back through the fiber-optic to a detector which can then quantify the fluorescence emission and convert the fluorescence into a molar concentration of the particular molecule. Often there is more than one molecule which is capable of fluorescing at the same wavelength as that of the molecule one wishes to detect and quantify. Thus, direct quantification is difficult, and requires expensive and time consuming separations methods for extracting interferant molecular species. Using an MHP FEP window on the fiber-optic can help to overcome this problem.

Depending on the transition metal and its catalytic properties, selective conversion of particular molecules within an analyte can be effected in cases where the conversion of the molecules results in a new molecule which can be either more easily detected by the particular sensing element employed, or in cases where the molecule is an interferant, can lose it fluorescent property and thus be eliminated from the analysis. For example, a pair of fiber-optic based sensors can be used in tandem such that one fiber has a window of an unmodified film of FEP and the other window has a film of FEP whose surface composition is comprised of iridium(I) covalently bonded to the FEP (i.e., an iridium MHP). The iridium MHP surface can effectively and selectively hydrogenate aromatic hydrocarbons (i.e., change a fluorescently active aromatic molecule like benzene into a fluorescently inactive non-aromatic molecule like cyclohexane). Thus, the fluorescence emission detected simultaneously from these two fiber-optic probes differs due to the loss of signal from benzene, for example, which upon approaching the MHP FEP is selectively catalyzed to non-aromatic cyclohexane which is not fluorescent. The difference in these signals can be quantified using appropriate calibration curves, and used to quantify either the concentration of benzene or the concentration of other aromatic hydrocarbons which were unaffected or resistant to hydrogenation by the iridium MHP. This can be accomplished without using any preliminary separation methods typically used to separate these molecular species before analysis.

Similarly, with filter applications one can take advantage of the non-fouling characteristics of the MHP of the invention for inhibiting clogging of pores which is a major limitation to other filters comprised of ceramic, inorganic, or organic polymeric material. Further, due to the greater thermal stability of MHP filters they can now be used in systems which heretofore were limited to filters fabricated from ceramic or inorganic materials. The MHP's as disclosed herein offer both these advantages in conjunction with their biocidal characteristics which are imparted from the transition metals covalently bonded to the fluoropolymer filters. For example, nylon, cellulose, and other polymeric filters have been coated or impregnated with transition metals like Ag, Cu, and Zn (Refs. Japanese Kokai, Tokkyo Koho JP, filed Nov 1, 1994, Application serial No. JP 94-39284; Japanese Kokai, Tokkyo Koho JP, filed Aug. 24, 1993, Application serial No. JP 92-19216; Japanese Kokai Tokkyo Koho JP, filed Feb. 25, 1991, Application serial No. JP 89-178864; Japanese Kokai, Tokkyo Koho JP, filed Mar. 8, 1991, Application serial No. JP 90-161744).

While the materials disclosed in the Japanese applications can operate effectively as biocidal air filters at ambient to slightly elevated temperatures, they have problems associated with leaching of the biocidal metals in aqueous environments. This presents not only ecological problems, but also the disadvantage of reduced life expectancy of the filter device, in addition to inherent fouling problems previously discussed. To overcome these problems ceramic filters with impregnated biocidal transition metals have been employed. However, problems related to leaching still occur as well as limitations due to cost, flexibility and fouling. Accordingly, the metallofluoropolymers of this invention provide advantages associated with their ability to withstand higher temperatures and the flexibility of being useful in air and aqueous environments. By covalently bonding transition metals, like Ag, Zn and Cu, a MHP based filter can be fabricated such that it functions as an effective non-fouling filter having biocidal characteristics without the problem of metal leaching occurring. The biocidally active MHPs containing Ag, Zn, Cu and mixtures of the same are also characterized as being cost effective, lightweight and flexible as compared to ceramic filters.

The following specific examples demonstrate the various aspects of the invention, however, it is to be understood that these examples are for illustrative purposes only, and do not purport to be wholly definitive as to conditions and scope.

EXAMPLE I $MoO_3$ has been demonstrated as a useful heterogeneous catalyst for converting propylene to acrolein, isobutene to acetone, methanol to formaldehyde, acrolein to acrylic acid, 1-butene to butadiene and maleic anhydride (*Catalysis at Surfaces*, by I. M. Campbell, published by Chapman and Hall, 1988 pg. 173.).

Part A

A 6 cm.×6 cm. piece of ePTFE with a pore size of 0.2 microns was measured by x-ray photoelectron spectroscopy (XPS) to have an elemental composition of 66% fluorine and 34% carbon. Subsequent exposure to a $H_2$/MeOH radio frequency glow discharge(RFGD) plasma for 5 minutes yielded a measured elemental composition of 57% carbon, 38% fluorine and 5% oxygen. The modified ePTFE was then refluxed in a $Mo(CO)_6$/benzene solution at 70° C. for 20 minutes. After removing the ePTFE film from the Mo solution it was ultrasonicated first in benzene for 5 minutes and then MeOH for 30 minutes. XPS measured an elemental surface composition of 63% carbon, 27% fluorine, 9% oxygen and 1% Mo. The binding energy as determined by XPS was 232.8 eV which relates to $MoO_3$ having an oxidation state of $Mo^{+6}$.

PART B

Alternatively, non-porous fluoropolymers like FEP can be metallized with Mo to provide flat sheets, beads, or particles of metallohalopolymers. For example, a 6 in x 6 in sheet of FEP analyzed by XPS was measured to have an elemental composition comprised of 69% fluorine and 31% carbon. Subsequent exposure to a $H_2$/MeOH RFGD plasma resulted in a surface having 36% fluorine, 58% carbon, and 6% oxygen. The modified fluoropolymer was then placed in a millimolar solution of $Mo(CO)_6$ in benzene and refluxed for 2 hours at 65° C. After removal from the solution the metallized FEP film was ultrasonically cleaned in pure benzene and analyzed by XPS. Results show that the original FEP material had been changed to a metallohalopolymer having an elemental composition of 32% fluorine, 51% carbon, 13% oxygen, and 4% Mo. The binding energy as corrected for Mo was 232.6 eV indicating catalytically active $MoO_3$ (i.e., $Mo^{+6}$ oxidation state) was covalently bonded and stable on the FEP surface.

PART C

Particles or beads of this metallohalopolymer (e.g., beads having a diameter of 5 microns in size) can then be used to fill a filter canister which can then be used to filter gases or liquids in such a way as to remove particulates and biological pathogens. Alternatively, this filter canister can be used for oxidizing an organic gas or liquid which is allowed to flow through the filter device. For example, propylene gas can be directed through the device containing the Mo metallohalopolymer beads in order to convert either all or a percentage of the propylene to acrolein.

EXAMPLE II

The superacidic nature of the oxygen functionality contained in the metallohalopolymers (MHPs) disclosed herein may be demonstrated through surface analysis of the following materials and subsequent treatments of the materials. For example, a 10 cm×10 cm film of FEP having a thickness of 100 microns was exposed to a RFGD plasma in the presence of a $H_2$/MeOH gas mixture at 100 mTorr pressure for 2 minutes. The resulting FEP film was analyzed by XPS which is a useful analytical method for determining the atomic composition of the top 10 nm of solid surfaces. XPS results of the unmodified FEP show an elemental atomic composition of 67% fluorine to 33% carbon which is stoichiometrically accurate with respect to the expected elemental composition of pure FEP. After the RFGD treatment as described above, the resulting XPS analysis showed the incorporation of oxygen functionality into the top 10 nm of the FEP film from the elemental percentages which were measured to be 44% carbon, 52.5% fluorine and 3.5% oxygen. This film was then subsequently treated by placing it into pure 18 molar $H_2SO_4$ for 24 hrs. followed by a thorough rinse in copious amounts of distilled water, followed by ultrasonication for 5 minutes in distilled water.

XPS analysis of this material measured a novel elemental composition containing 50% carbon, 40% fluorine, 7.5% oxygen, and 1.5% sulfur. The sulfur binding energy was corrected to 169.1 eV which is consistent with a highly oxidized sulfur. The resulting oxygen to sulfur ratio (O/S) =5:1 is consistent with a protonated $H_3SO_4^+$ which is then ionically bonded to the negatively charged oxygen site (created from the loss of the hydrogen to the $H_2SO_4$) on the modified FEP surface. In other words, if $H_2SO_4$ was only adventitiously adsorbed it would easily wash off the surface during the described rinse procedure (as determined through experiments using unmodified FEP in which no incorporation of sulfur was measured by XPS). By protonating the $H_2SO_4$ to $H_3S_4^+$ a simultaneous creation of a positively charged $H_3SO_4^+$ ion and a $O^-$ negative site on the modified FEP surface leads to an ionic bond formation between $H_3SO_4^+$ and FEP-$O^-$. This mechanism is supported by XPS results which measure a 5:1 O/S ratio which is consistent with the expected stoichiometry of a surface having a protonated sulfuric acid ionically bonded to negatively charged oxygen sites on an FEP surface.

EXAMPLE III

PART A

Vanadium(V) also has the ability for achieving or performing oxidations on organic and biological molecules. Vanadium was covalently bonded to fluoropolymers (porous ePTFE or non-porous FEP) with the objective of synthesizing a metallohalopolymer according to the invention. A 5 in.×5 in. sheet of porous ePTFE having an initial elemental composition (determined by XPS) of 66% fluorine and 34% carbon was modified by a 7 minute exposure to $H_2$/MeOH RFGD plasma. The resulting elemental composition as determined by XPS was 44% fluorine, 48% carbon and 8% oxygen. The modified fluoropolymer was then treated with $VOCl_3$ vapor at 65° C. for 30 min. After ultrasonically cleaning first in hexane and then in ethanol (1 min. for each solvent) XPS showed the covalent incorporation of vanadium forming a metallohalopolymer composition with 24% fluorine, 37% carbon, 28% oxygen, and 11% vanadium. The binding energy of the vanadium was corrected to 518.5 eV indicating a high valent vanadium ($V_2O_5$) in its +5 oxidation state.

PART B

Similar to molybdenum, vanadium is a useful metal for oxidatively killing aerobic biological pathogens (e.g., bacteria and fungi) and catalyzing oxidative transformations of organic molecules. For example, either a direct flow through filter comprised of parallel porous sheets of a vanadium metallohalo-ePTFE material can be used for filtering liquids or gases of particulates and for killing unwanted pathogens.

Alternatively, a filter based on percolation through a canister filled with particles or beads of FEP could also achieve the desired filtration and antipathogenic results useful for a given application. Further, vanadium is a useful metal for catalyzing the conversion of acrolein to acrylic acid (among other organic transformations), and thus, similar devices as those described for filtration can be constructed to allow flow of acrolein, (or other organic molecule to be oxidized), through either a porous membrane of a vanadium MHP or through percolation through a bed of vanadium particles or beads (such as FEP) in order to produce total or partial conversion of acrolein to acrylic acid. This is just one example of using vanadium as a catalyst according to the present invention.

EXAMPLE IV

An example of converting FEP to a vanadium MHP was achieved by using a 6 in.×6 in. piece of modified FEP having the same elemental composition as that in Example I, Part B. After the RFGD modification the FEP was exposed to $V(O)Cl_3$ vapor at room temperature for 30 min., baked for 10 min. at 150° C., and then ultrasonically cleaned for 30 min. in MeOH. The resulting composition was comprised of 23% fluorine, 28% carbon, 41% oxygen and 8% vanadium. The binding energy corrected for vanadium was 518.5 eV which was identical to the vanadium MHP formed using the porous ePTFE, and similarly indicates a high oxidation state of +5 for the vanadium species bonded to the fluoropolymer surface.

EXAMPLE V

The above examples illustrate the ability to covalently bond transition metals to halopolymers with the added feature of stabilizing them in high oxidation states. Transition metals bonded in this fashion can also be reduced to lower oxidation states including zero valent conducting metallic films. This can be achieved by using appropriate reducing agents or deposition conditions. In this example, the invention is illustrated by methods which covalently bond Rhodium (Rh) in a controlled manner to achieve either a +3 or zero valent oxidation state.

PART A

Two methods for covalently bonding Rh in an oxidation state of +3 were accomplished by using a porous fluoropolymer film of ePTFE. A sheet of porous ePTFE having the same elemental composition as that in Examples I (Part A) and III (Part A) was modified by exposure to a $H_2$/MeOH RFGD plasma. The resulting film had the same elemental compositions as those demonstrated in Example I, Part A. After cutting the film in half giving two 3 in×3 in films, one was placed in a millimolar solution of $RhCl_3$ in $H_2O$ at 65° C. for 2 hrs., and the other in a millimolar solution of $RhCl_3$ in $H_2O$, plus one drop of 2,6, lutadine at 65° C. for 1 hr. Both films were ultrasonically cleaned in $H_2O$ for 30 min and analyzed by XPS. In the case of the deposition without 2,6, lutadine the elemental composition was measured to be 38% fluorine, 50% carbon, 10% oxygen and 2% rhodium. In the case where lutadiene was added, the elemental compositions were measured to be 32% fluorine, 39% carbon, 23% oxygen and 6% rhodium. In both cases the binding energy of rhodium was corrected to 309.5 eV which indicates that the rhodium was in an oxidation state of +3.

PART B

Alternatively, an identical piece of ePTFE was placed in a millimolar solution of $RhCl_3$ in EtOH at 70° C. for 12 hrs. After ultrasonically cleaning the film in EtOH for 30 min a thin shiny metallic film remained which was analyzed to be pure Rh with a corrected binding energy of 308.0 eV. This is indicative of a zero valent metallic rhodium film. Further, a Scotch® tape test was performed and no removal of the Rh film was observed indicating the initial covalent attachment of Rh to the oxygen sites on the modified fluoropolymer with subsequent growth of a Rh metal film.

PART C

Rhodium is well known to be a good catalyst for promoting the hydrogenation of alkenes and various alcohols, and is also well known for its use in Ziegler-Natta type catalysis for polymerization of alkenes. Further, Rh in a zero oxidation state has also found utility as a catalyst used in the construction of catalytic converters for the automobile industry. These uses are only illustrative of the utility of Rh and not wholly inclusive of all its possible applications. For practical purposes, Rh can be covalently bonded to either porous fluoro- or fluorochloropolymer materials or to non-porous fluoro- and fluorochloropolymers and then utilized similarly for applications disclosed in Examples I and III.

EXAMPLE VI

As described in Examples I and III, metals which catalyze oxidations, like Mo, can have antipathogenic properties which makes fluoro- and fluorochloropolymers having these metals covalently bonded useful as filters and materials used for controlling and inactivating pathogens which come in contact with them. Alternatively, metals like Ag, Zn, and Cu have also demonstrated antipathogenic activity possibly due to their ability to cycle between an oxidized and reduced state which is related to their small redox potential. Accordingly, MHPs (either porous, or non-porous) comprising Ag, Zn, and Cu would also be useful as solid catalysts and as biocidal filters. Methods for preparing such MHPs by the steps of covalently bonding these metals may be performed in accordance with the following protocol:

PART A

FEP beads having diameters of 10 microns were analyzed by XPS and measured to have an elemental composition of 69% fluorine and 31% carbon. A 10 cm$^3$ volume of the beads was placed into an RFGD plasma generator and exposed to a $H_2$/MeOH plasma at 100 mTorr pressure for 5 minutes. A sample of the beads was analyzed by XPS and shown to have an elemental composition of 46% fluorine, 48% carbon and 6% oxygen. The beads were then placed for 12 hrs in 100 ml of MeOH containing millimolar concentration of $AgNO_3$. After removing them from solution they were ultrasonically cleaned in MeOH for 30 min. and then analyzed by XPS. XPS results showed the surfaces of the beads with an elemental composition of 17% fluorine, 70% carbon, 10% oxygen and 3% Ag. The corrected binding energy of Ag was measured to be 369.0 eV, which represents covalently bonded $Ag^{+1}$.

PART B

A modified sheet of porous ePTFE similar in elemental composition as that described in Examples I and III was placed in a solution of diethyl ether containing millimolar amounts of $AgNO_3$ for 3 days at room temperature. XPS showed the covalent incorporation of silver forming a metallohalopolymer composition which had 24% fluorine, 37% carbon, 28% oxygen and 11% silver. The corrected binding energy of the silver was 368.0 eV indicating the covalent bonding of zero valent silver metal using these conditions. This illustrates the ability to control the oxidation state of silver by changing the deposition solution from MeOH to diethyl ether (i.e., we observed $Ag^{+1}$ from the MeOH solution and $Ag^0$ from the diethyl ether solution).

Besides being a useful biocidal agent, silver also has catalytic activities useful for oxidizing organic molecules. For example, silver provides the unique catalysis and high selectivity for converting ethylene to ethylene oxide. This is used extensively in industrial applications which would benefit greatly with respect to using a fluoropolymer solid support containing catalytically active silver.

EXAMPLE VII

As previously mentioned, Cu also has good biocidal characteristics, as well as catalytic activities for decomposing formic acid and oxidizing methanol, among other catalytic uses.

FEP beads having diameters of 500 microns were treated and modified as described in Example VI. XPS results showed elemental compositions after a RFGD plasma treatment of 40% fluorine, 54% carbon and 5% oxygen. The modified FEP beads were then placed in a 0.5M $NH_4OH$ in $H_2O$ solution containing millimolar concentrations of CuSCN for 2 hrs at room temperature. After removal, the beads were ultrasonically cleaned in distilled $H_2O$ for 30 minutes and analyzed by XPS. Results showed the incorporation of covalently bonded Cu from the elemental composition which was measured to be 19% fluorine, 65% carbon, 13% oxygen and 3% copper. The binding energy of copper was corrected to be 934.8 eV which indicates that the copper was bonded in a stable +1 oxidation state which is catalytically active for selective oxidation of a variety of organic molecules including ethylene to ethylene oxide.

EXAMPLE VIII

As described above, Zn also has good biocidal characteristics, as well as catalytic activities. For example, ZnO in the presence of Cu is useful for catalytically converting $CO+2H_2$ to $CH_3OH$. An example of constructing a useful catalytic device would first utilize the formation of ZnO covalently bonded to either a porous ePTFE or a non-porous solid fluoropolymer.

Formation of ZnO onto a fluoropolymer was achieved by reacting a sheet (6 cm×6 cm) of modified ePTFE (having an elemental composition similar to those described in Examples I and III), with $ZnCl_2$ in dimethylformamide (1 millimolar) which was refluxed for 1 hr. After removing the ePTFE sheet it was ultrasonically cleaned in DMF for 30 min. then soaked in MeOH for 24 hrs. XPS measured an elemental composition for the resulting metallohalopolymer to be 33% fluorine, 46% carbon, 13% oxygen and 8% zinc. The binding energy of zinc was corrected to be 1023.4 eV which relates to $Zn^{+2}$ or ZnO covalently bonded to the fluoropolymer surface. This porous MHP can then be vapor coated with copper, pleated and formed within a filter canister, (or in the case of FEP beads the canister can be filled with the MHP beads), which is filled with a flowing mixture of CO and $H_2$ gases at appropriate temperature and pressure. Upon contact with the ZnO/Cu MHP the CO and $H_2$ can react to form MeOH liquid which can be collected through a vent leading out of the filter canister. This apparatus can also be used to effectively filter bacteria from air or water.

EXAMPLE IX

As previously pointed out, many of the transition metals play important roles as catalytic agents. Accordingly, MHPs comprising such transition metals can be prepared by covalently bonding a variety of transition metals to fluoro- or fluoro-chloropolymers by the following methods.

$Co^{+2}$ Metallohalopolymer

A sheet of porous ePTFE was analyzed by XPS to have an elemental composition of 67% fluorine and 33% carbon. A 6 cm×6 cm piece of the ePTFE was cut and treated by exposure to a $H_2$/MeOH plasma at 100 mTorr for 5 min. XPS measured an elemental composition of 40% fluorine, 55% carbon and 5% oxygen on the modified ePTFE. The sheet of ePTFE was then placed into a millimolar solution of $CoCl_2$ in dimethylformamide and refluxed for 1.5 hrs. After removing the sheet of ePTFE it was ultrasonically cleaned in dimethylformamide for 10 min. and washed in distilled $H_2O$. XPS was then used to measure an elemental composition of 36% fluorine, 54% carbon, 7% oxygen and 3% cobalt. The corrected binding energy of the covalently bonded cobalt was measured to be 782.0 eV which relates to an oxidation state of +2.

$Ti^{+4}$ Metallohalopolymer

A piece of porous ePTFE prepared in the same manner as described in connection with preparation of $Co^{+2}$ MHP was exposed to $TiCl_4$ vapor for 2 hrs. After soaking in MeOH for 24 hrs the material was analyzed by XPS and shown to be comprised of an elemental composition containing 37% fluorine, 50% carbon, 10% oxygen and 3% titanium. The corrected binding energy of the titanium was 459.7 eV and indicated the covalent attachment of $Ti^{+4}$.

$Cr^{+6}$ Metallohalopolymer

A piece of non-porous FEP was analyzed by XPS. The measured elemental composition was 68% fluorine and 32% carbon. A 6 cm×6 cm piece of the FEP was cut and treated with a $H_2$/MeOH rfgd plasma for 3 min. The resulting elemental composition as determined by XPS analysis was 52% fluorine, 45% carbon and 3% oxygen. This material was then placed into a millimolar solution of $Cr(C_6H_6)(CO)_3$ in benzene for 1 hr. at 65° C. followed by 3 hrs at room temperature. After removing the FEP, it was ultrasonically cleaned in benzene for 30 min. and analyzed by XPS. Results showed a composition of matter comprising 49% fluorine, 43% carbon, 6% oxygen and 2% chromium. The corrected binding energy of chromium was 577.7 eV indicating $CrO_3$ or $Cr^{+6}$.

$W^{+6}$ Metallohalopolymer

A modified piece of FEP similar to that described in the synthesis of the $Cr^{+6}$ MHP above was placed into a millimolar solution of $WCl_6$ in diethyl ether for 8 days at room temperature. After removing and ultrasonically cleaning the material in MeOH for 30 min. the material was analyzed by XPS. The resulting elemental composition of the material was found to be 8% fluorine, 76% carbon, 12% oxygen, 2% tungsten and 2% chlorine. The corrected binding energy of the tungsten was 36.0 eV indicating a covalently bonded tungsten in a +6 oxidation state.

$Pd^{+2}$ Metallohalopolymer

A modified piece of FEP similar to that described in preparation of the $Cr^{+6}$ MHP above was placed into 0.1M HCl with a millimolar concentration of ammonium tetrachloropaladate for 24 hrs. After removing the FEP material it was ultrasonically cleaned in distilled $H_2O$ for 30 min. and analyzed by XPS. The resulting composition of matter was 14% fluorine, 69% carbon, 14% oxygen and 3% palladium. The corrected binding energy of the palladium was 338.0 eV indicating a covalently bonded palladium in a +2 oxidation state.

$Pd^0$ Metallohalopolymer

A modified piece of ePTFE similar to that in the Example relating to cobalt was placed into 100 ml of a millimolar solution of $Pd(OAc)_2$ in benzene at 75° C. for 24 hrs. After removing the ePTFE it was ultrasonically cleaned in pure benzene for 1 hr and then rinsed with distilled water, dried and analyzed by XPS. The resulting composition of matter was 17% fluorine, 63% carbon, 15% oxygen, and 5% palladium. The corrected binding energy of the palladium was 336.0 eV indicating a metallic Pd° oxidation state.

$Ir^{+3}$ Metallohalopolymer

A modified piece of FEP similar to that described in the synthesis of $Cr^{+6}$ MHP was placed into 100 ml of a millimolar solution of Iridium carbonyl ($Ir_4(CO)_{12}$) in dry toluene and refluxed for 1 hr under an inert $N_2$ atmosphere. After removal the FEP was ultrasonicated for 30 min. in pure toluene, dried and analyzed by XPS. The resulting composition of matter was 10% fluorine, 68% carbon, 14% oxygen, and 8% iridium. The corrected binding energy of the iridium was 63.8 eV indicating that $Ir^{+3}$ was bonded to the FEP surface.

$Mo^{+6}$ Metallohalopolymer

A 6 cm.×6 cm. piece of ePTFE with a pore size of 0.2 microns was measured by XPS to have an elemental composition of 66% fluorine and 34% carbon. Subsequent exposure to a $H_2$/MeOH RFGD plasma for 5 minutes yielded a measured elemental composition of 57% carbon, 38% fluorine and 5% oxygen. The ePTFE was then exposed to $PBr_3$ vapor for 10 min., removed and then baked at 110° C. for 20 min., rinsed in distilled water and then analyzed by XPS. The resulting composition of matter comprised 57% carbon, 30% fluorine, 9% oxygen, and 4% phosphorous indicating the formation of an ePTFE-P-O surface. The ePTFE was then placed into 100 ml of a millimolar solution of $Mo(CO)_6$ in benzene at 65° C. for 1 hr. After removing the sample from the benzene solution it was ultrasonically cleaned in pure benzene for 10 min., washed with distilled water and analyzed by XPS. The resulting composition of matter was 62% carbon, 12% fluorine, 20% oxygen, 4% phosphorous, and 2% molybdenum. The corrected binding energy of the Mo was 134.5 indicating the covalent attachment of $Mo^{+6}$ to an ePTFE-P-O MHP.

$RU^{+3}$ Metallohalopolymer

A 6 cm.×6 cm. piece of ePTFE with a pore size of 0.2 microns was measured by XPS to have an elemental composition of 66% fluorine and 34% carbon. Subsequent exposure to a $H_2$/MeOH RFGD plasma for 5 minutes yielded a measured elemental composition of 57% carbon, 38% fluorine and 5% oxygen. The ePTFE was then exposed to $SiCl_4$ vapor for 15 min. and then baked at 110° C. for 5 min. The sample was then ultrasonically cleaned in MeOH for 30 min., washed with distilled water, and then analyzed by XPS. The resulting composition of matter comprised 43% carbon, 19% fluorine, 29% oxygen and 9% silicon indicating the formation of a ePTFE-Si-O surface. This material was then placed into a millimolar solution of $RuCl_3$ in ethanol for 6 hrs at room temperature. After removing the material it was ultrasonically cleaned in ethanol for 30 min., dried and analyzed by XPS. The resulting composition of matter comprised 59% carbon, 14% fluorine, 18% oxygen, 6% silicon, and 3% ruthenium. The corrected binding energy of the Ru was 456.2 eV indicated $Ru^{+3}$ was covalently bonded to the ePTFE-SiO MHP.

The invention has been described in conjunction with specific examples thereof. They are illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

We claim:

1. A metallohalopolymer, which comprises a halogenated polymer having an outer surface modified with hydrogen and oxygen or oxygen-containing groups substituted for at least a portion of the halogen atoms thereon to provide an oxyhalopolymer, the oxygen or oxygen-containing groups on said oxyhalopolymer modified with an amount of covalently bonded transition metal on the outermost surface of said oxyhalopolymer and to depths of up to about 200 Å to provide a surface having catalytic activity related to that of the particular transition metal, wherein the bulk characteristics of the halogenated polymer are retained below the modified outer surface region of the metallohalopolymer.

2. The metallohalopolymer of claim 1 wherein the oxygen or oxygen-containing groups are modified by the introduction of the transition metal as covalently bonded metals in predetermined oxidation states or covalently bonded conductive metallic film.

3. The metallohalopolymer of claim 1 wherein said oxyhalopolymer is an oxyfluoropolymer or oxychlorofluoropolymer.

4. The metallohalopolymer of claim 2 comprising repeating non-terminal units selected from the group consisting of:

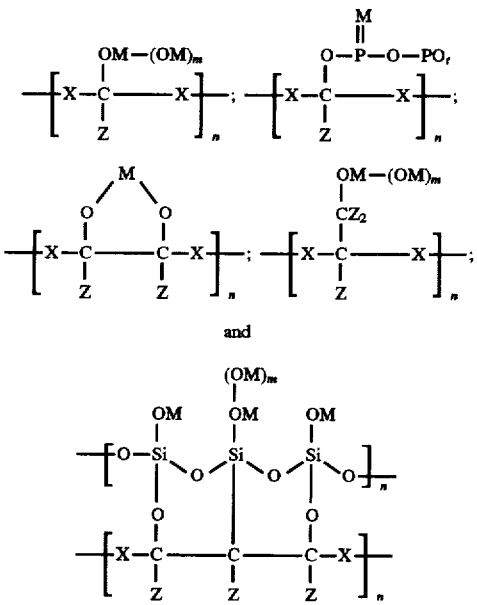

and

Wherein M is a transition metal; Z is fluorine, chlorine, hydrogen, or O—R where R is hydrogen, —$(CH_2)_y$, —$CH_3$ or —$CH_3$ where y=1 to 20; X is $CF_2$, CFCl, $CCl_2$, CFH, CClH or $CH_2$; n=10 to 1000, t=2 to 3 and m=0 to 1000.

5. The metallohalopolymer of claim 2 wherein from about 1 to about 100 percent of the oxygen or oxygen-containing groups of the outermost surface of said oxyhalopolymer and to depths ranging from about 10 to about 200 Å have covalently bonded thereto a transition metal (M) selected from the group consisting of Group IIIa, IVa, Va, VIa, VIIa, VIIIa, Ib, IIb, IIIb and IVb of the Periodic table.

6. The metallohalopolymer of claim 2 wherein from about 1 to about 90 percent of the surface halogen atoms of said halogenated polymer are permanently substituted with hydrogen and oxygen or oxygen-containing groups from which about 30 to about 100 percent of the substituted halogens are replaced with oxygen or oxygen-containing groups and from about 0 to about 70 percent of said substituted halogens are replaced with hydrogen atoms, and where from about 1 to about 100 percent of said surface oxygen or oxygen-containing groups have covalently bonded thereto a transition metal selected from the group consisting of Group IIIa, IVa, Va, VIa, VIIa, VIIIa, Ib, IIb, IIIb and IVb of the Periodic Table.

7. The metallohalopolymer of claim 4 wherein the transition metal is a member selected from the group consisting of Group IIIa, IVa, Va, VIa, VIIa, VIIIa, Ib, IIb, IIIb and IVb of the Periodic Table.

8. The metallohalopolymer of claim 4 wherein the halogenated polymers are selected from the group consisting of polytetrafluoroethylene, expanded polytetrafluoroethylene, polychlorotetrafluoroethylene, polyvinylidene fluoride and polyvinyl fluoride and fluorinated ethylene-propylene copolymer.

9. A catalytic composition comprising the metallohalopolymer of claim 4.

10. A biocidal composition comprising the metallohalopolymer of claim 4.

11. A filtration device comprising a biocidally effective amount of the composition of claim 10.

12. A metallohalopolymer, which comprises an oxyhalopolymer prepared from a halogenated polymer, said oxyhalopolymer selected from the group consisting of an oxyfluoropolymer and an oxychlorofluoropolymer, said oxyhalopolymer having an outer surface modified wherein from about 1 to about 100 percent of the oxygen or oxygen-containing groups of the outermost surface and to depths ranging from about 10 to about 200 Å have covalently bonded thereto a transition metal or covalently bonded conductive metallic film.

13. The metallohalopolymer of claim 12 comprising repeating non-terminal units selected from the group consisting of:

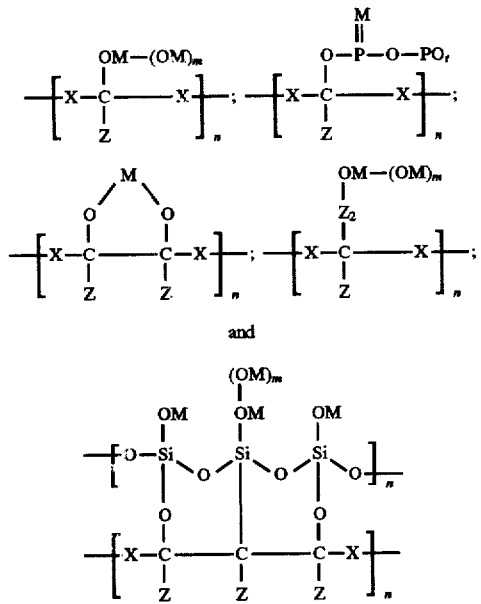

Wherein M is a transition metal; Z is fluorine, chlorine, hydrogen, —(CH$_2$)$_y$—CH$_3$, —CH$_3$, or O—R where R is hydrogen, —(CH$_2$)$_y$—CH$_3$ or —CH$_3$ where y is 1 to 20; X is CF$_2$, CFCl, CCl$_2$, CFH, CClH or CH$_2$, n=10 to 1000, t=2 to 3 and m=0 to 1000.

14. The metallohalopolymer of claim 13 wherein the transition metal (M) is a member selected from the group consisting of Group IIIa, IVa, Va, VIa, VIIa, VIIIa, Ib, IIb, IIIb and IVb of the Periodic Table.

15. The metallohalopolymer of claim 14 wherein the perhalocarbon and halohydrocarbon polymers are selected from the group consisting polytetrafluoroethylene, expanded polytetrafluoroethylene, fluorinated ethylenepropylene copolymer, polychlorotrifluoroethylene, polyvinylidene fluoride and polyvinyl fluoride, polyvinyl chloride, and polyfluoro-alkoxy polymer.

16. A metallohalopolymer comprising a halogenated polymer with an oxyhalopolymer outer surface and a transition metal covalently bonded directly to a reactive oxygen site on said oxyhalopolymer.

17. The metallohalopolymer of claim 16 wherein the transition metal is present as covalently bonded metals in predetermined oxidation states or a covalently bonded metallic film.

18. The metallohalopolymer of claim 17 wherein the oxyhalopolymer is an oxyfluoropolymer or an oxychlorofluoropolymer.

19. The metallohalopolymer of claim 17 wherein the oxyhalopolymer is derived from a polymer selected from the group consisting of perhalocarbon polymer, a halohydrocarbon polymer, or a polyfluoroalkoxy polymer.

20. The metallohalopolymer of claim 19 wherein perhalocarbon polymer is tetrafluoroethylene, expanded tetrafluoroethylene, polychlorotrifluoroethylene or fluorinated ethylene-propylene copolymer, and the halohydrocarbon polymer is polyvinyl fluoride, polyvinylidene fluoride or polyvinyl chloride.

21. The metallohalopolymer of claim 19 comprising repeating non-terminal units selected from the group consisting of:

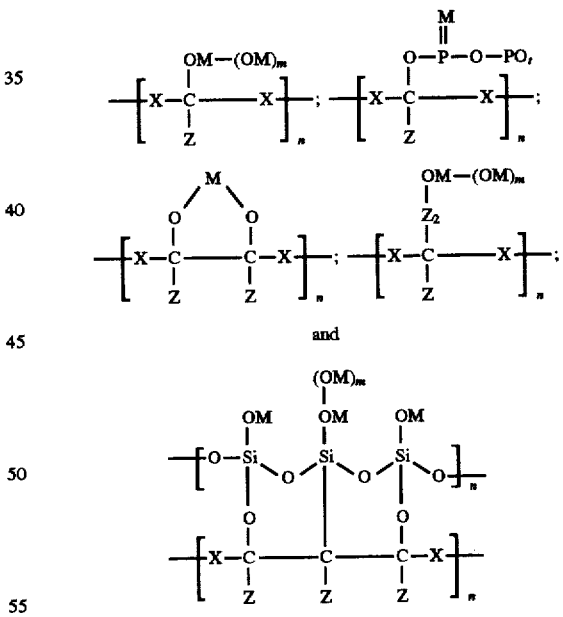

Wherein M is a transition metal; Z is fluorine, chlorine, hydrogen, —(CH$_2$)$_y$—CH$_3$, —CH$_3$ or O—R where R is hydrogen, —(CH$_2$)$_y$—CH$_3$ or —CH$_3$ where y is 1 to 20, X is CF$_2$, CFCl, CCl$_2$, CFH, CClH or CH$_2$, n=10 to 1000, t=2 to 3 and m=0 to 1000.

22. The metallohalopolymer of claim 16 wherein the halogenated polymer comprises a carbon backbone with halogen atoms and optionally one or more members selected from the group consisting of carbon, hydrogen and oxygen.

23. The metallohalopolymer of claim 16 wherein the halogenated polymer comprises a silicon backbone with halogen atoms and optionally one or more members selected from the group consisting of carbon, hydrogen and oxygen.

24. The metallohalopolymer of claim 16 wherein the halogenated polymer comprises a phosphorus backbone with halogen atoms and optionally one or more members selected from the group consisting of carbon, hydrogen, oxygen and nitrogen.

25. A catalytic composition comprising the metallohalopolymer of claim 16.

26. A biocidal composition comprising the metallohalopolymer of claim 16.

27. A filtration device comprising a biocidally effective amount of the composition of claim 26.

28. A sensor probe comprising the metallohalopolymer of claim 16.

29. A method of synthesizing metallohalopolymers which comprises the steps of:

(a) providing a halogenated polymer;

(b) modifying the halogenated polymer of (a) by a method selected from the group consisting of (i) radio frequency glow discharge of hydrogen/methanol gas-vapor under vacuum, (ii) wet chemical reduction and (iii) exposing to actinic radiation in the presence of oxygen containing organic modifiers to substitute at least a portion of the halogen atoms with hydrogen and oxygen or oxygen-containing groups on the outermost surface of said halogenated polymer and to depths of up to about 200 Å to provide an oxyhalopolymer, and (c) contacting the oxyhalopolymer of (b) with a solution or gas comprising transition metal complexes for a sufficient time period to facilitate covalently bonding thereto a transition metal or covalently bonded conductive metallic film.

30. The method of claim 29 wherein from about 1 to about 100 percent of the oxygen or oxygen-containing groups of the outermost surface of said oxyhalopolymer to depths ranging from about 10 to about 200 Å have covalently bonded thereto a transition metal (M) selected from the group consisting of Group IIIa, IVa, Va, VIa, VIIa, VIIIa, Ib, IIb, IIIb and IVb of the Periodic table.

31. The method of claim 30 wherein from about 1 to about 90 percent of the surface halogen atoms of said halopolymer including halogens to depths from about 10 to about 200 Å are permanently substituted with hydrogen and oxygen or oxygen-containing groups from which about 30 to about 100 percent of the substituted halogens are replaced with oxygen or oxygen-containing groups and from about 0 to about 70 percent of said substituted halogens are replaced with hydrogen atoms, and where from about 1 to about 100 percent of said surface oxygen or oxygen-containing groups have covalently bonded thereto a transition metal selected from the group consisting of Group IIIa, IVa, Va, VIa, VIIa, VIIIa, Ib, IIb, IIIb and IVb of the Periodic table.

* * * * *